(12) United States Patent
Carrasco González

(10) Patent No.: US 10,842,827 B2
(45) Date of Patent: Nov. 24, 2020

(54) TREATMENT AND COMPOUND FOR EPITHELIAL WOUNDS

(71) Applicant: José Manuel Aguilar Yáñez, Ensenada (MX)

(72) Inventor: Jorge Alberto Carrasco González, Nuevo León (MX)

(73) Assignee: José Manuel Aguilar Yáñez, Ensenada (MX)

( * ) Notice: Subject to any disclaimer, the term of this patent is extended or adjusted under 35 U.S.C. 154(b) by 0 days.

(21) Appl. No.: 16/248,675

(22) Filed: Jan. 15, 2019

(65) Prior Publication Data

US 2020/0061125 A1 Feb. 27, 2020

Related U.S. Application Data

(60) Provisional application No. 62/721,154, filed on Aug. 22, 2018.

(51) Int. Cl.
| | |
|---|---|
| *A61K 35/644* | (2015.01) |
| *A61P 17/02* | (2006.01) |
| *C07K 14/435* | (2006.01) |
| *A61K 9/12* | (2006.01) |
| *A61K 9/00* | (2006.01) |
| *A61K 9/06* | (2006.01) |

(52) U.S. Cl.
CPC ............ *A61K 35/644* (2013.01); *A61P 17/02* (2018.01); *C07K 14/43572* (2013.01); *A61K 9/0014* (2013.01); *A61K 9/0019* (2013.01); *A61K 9/0053* (2013.01); *A61K 9/06* (2013.01); *A61K 9/12* (2013.01)

(58) Field of Classification Search
CPC .................................................. A61K 35/644
See application file for complete search history.

(56) References Cited

U.S. PATENT DOCUMENTS

| | | | |
|---|---|---|---|
| 2015/0030688 A1* | 1/2015 | Sell ........................ | A61K 38/18 424/537 |
| 2016/0324976 A1* | 11/2016 | Lee ......................... | C07K 7/06 |
| 2017/0190748 A1* | 7/2017 | Johnson ............. | C07K 14/8139 |

FOREIGN PATENT DOCUMENTS

WO 2015/164981 A1 11/2015

OTHER PUBLICATIONS

USPTO/ISA, International Search Report and Written Opinion for PCT Application No. PCT/US19/30054, dated Sep. 13, 2019.
Ochiai et al., "Transplanted mesenchymal stem cells are effective for skin regeneration in acute cutaneous wounds of pigs." Regen Ther, Jul. 4, 2017, vol. 7, pp. 8-16.
Cox-Foster et al., "A Metagenomic Survey of Microbes in Honey Bee Colony Collapse Disorder", article, www.sciencemag.org, Science, vol. 318, published Oct. 12, 2007, Downloaded from http://science.sciencemag.org/ on Nov. 13, 2018. pp. 283-288.
Bucekova et al. "Bee-derived antibacterial peptide, defensin-1, promotes wound reepithelialisation in vitro and in vivo", article, Scientific Reports, Published online Aug. 4, 2017, 13 total pages.
Driver et al., "The costs of diabetic foot: The economic case for the limb salvage team", Journal, Journal of Vascular Surgery, vol. 52, No. 12S, Published Sep. 2010, 6 total pages.
Leitai et al, "Investigation of the Use of Honey Bees and Honey Bee Products to Assess Heavy Metals Contamination", Journal, Environmental Monitoring and Assessment, Oct. 1996, vol. 43, Issue 1, pp. 1-9.
Department of Biochemistry, University of Medicine-Magway, Magway, Myanmar, "Pharmacological effects of Royal Jelly on Human Skin", article, Pharamacological and Pharmaceutical Reports, Published May 8, 2018, 4 total pages.
Siavash et al., "The efficacy of topical Royal Jelly on diabetic foot ulcers healing: A case series", Journal, The efficacy of topical Royal Jelly on diabetic foot ulcers healing: A case series, J Res Med Sci. Jul. 2011; 16(7): 904-909, https://www.ncbi.nlm.nih.gov/pmc/articles/PMC3263103/?report=printable, last accessed Nov. 13, 2018.
Siavash et al., "The efficacy of topical royal jelly on healing of diabetic foot ulcers: a double-blind placebo-controlled clinical trial", Journal, International Wound Journal ISSN 1742-4801, published Apr. 8, 2013, 6 total pages.

\* cited by examiner

*Primary Examiner* — Amy L Clark
(74) *Attorney, Agent, or Firm* — SoCal IP Law Group LLP; Brian S. Tamsut; Steven C. Sereboff

(57) ABSTRACT

There are disclosed an effective dosage of major royal jelly protein 1 for treating various skin ailments. Instead of administering royal jelly, an effective amount of the active constituent of royal jelly, MRJP1 is administered either alone or in combination with other topical pharmaceuticals.

2 Claims, 3 Drawing Sheets

Specification includes a Sequence Listing.

TREATMENT AND COMPOUND FOR EPITHELIAL WOUNDS

RELATED APPLICATION INFORMATION

This patent claims priority from Application No. 62/721,154 filed Aug. 22, 2018 entitled "Pharmaceutical formulations comprising royal jelly protein concentrated, methods for their preparations and uses thereof".

NOTICE OF COPYRIGHTS AND TRADE DRESS

A portion of the disclosure of this patent document contains material which is subject to copyright protection. This patent document may show and/or describe matter which is or may become trade dress of the owner. The copyright and trade dress owner has no objection to the facsimile reproduction by anyone of the patent disclosure as it appears in the Patent and Trademark Office patent files or records, but otherwise reserves all copyright and trade dress rights whatsoever.

SEQUENCE LISTING

The instant application contains a Sequence Listing which has been submitted in ASCII format via EFS-Web and is hereby incorporated by reference in its entirety. Said ASCII copy, created on Mar. 5, 2019 is named TREATMENT AND COMPOUND FOR EPITHELIAL WOUNDS ST25.txt and is 11,151 bytes in size.

BACKGROUND

Field

This disclosure relates to a method of use and preparation of compounds for treating epithelial wounds, or skin wounds.

Description of the Related Art

Each year millions of people suffer from severe skin wounds. These wounds sometimes never heal, never heal fully, or if they do heal take years to reach full recovery. Skin wounds may appear as a disorder in of themselves or be a byproduct of other diseases. For example, common diseases such as diabetes (which affects nine percent of the world population) and vascular diseases (pressure wounds, gangrene etc.) decrease life expectancy and may lead to skin wounds. Worse yet, these skin wounds may lead to limb amputation. As of 2013, the United States spent $116 billion on treating diabetes and its related complications. 33% of this budget went to researching the common skin wound associated with diabetes, foot ulcers. [Driver et al., 2010].

Royal jelly is a bee secretion used for the nutrition of larvae and queen bees. It has historically been used as a remedy in wound healing. Its perceived success is believed to be due to its antibacterial, anti-inflammatory, and immunomodulatory activities. Some believe that royal jelly exhibits different biological activities when exposed to different cell types. Others believe that royal jelly does not heal anything. In fact, some government authorities such as the European Food Safety Authority, and United States FDA have stated there is no evidence that royal jelly has any benefits. Clinical studies in humans evaluating the effectiveness of royal jelly have found little to no positive effect. Time and time again when researchers treat different test subjects with royal jelly formulations, they either report no positive results, or minute recovery that may not even be attributable to the application of the royal jelly.

The problem is further complicated by environmental factors having both direct and indirect effects on apiculture. The apiculture industry faces a decline in the number of bees each year due to environmental factors such as global warming and beehive collapse disorder. A reduction in bees means there are less hives capable of producing royal jelly. Increased use of chemicals including herbicides, pesticides and fertilizers adversely affects the production of royal jelly, as these chemicals have made their way into bee habitats. These chemicals can contaminate bee products, including royal jelly. Already, reports show that royal jelly and honey have been contaminated with heavy metals and other undesirable compounds which make royal jelly unstable and unsuitable for medicinal purposes. [Cox-Foster et al., 2017], [Bogdanov et al., 2006], [Leita G et al. 1996]. Furthermore, besides positive antibacterial effects, the scientific literature has failed to identify any proteins or chemicals in royal jelly responsible for any other perceived benefits.

Major royal jelly proteins are a family of proteins secreted by bees. Currently there are nine known proteins in the major royal jelly protein family. The distribution of major royal jelly protein type 1 to 9 is almost never uniform in major royal jelly production. Additionally, royal jelly contains other chemicals besides major royal jelly proteins such as vitamins, sugars, fats, enzymes, and other proteins.

DETAILED DESCRIPTION

Figure 1:
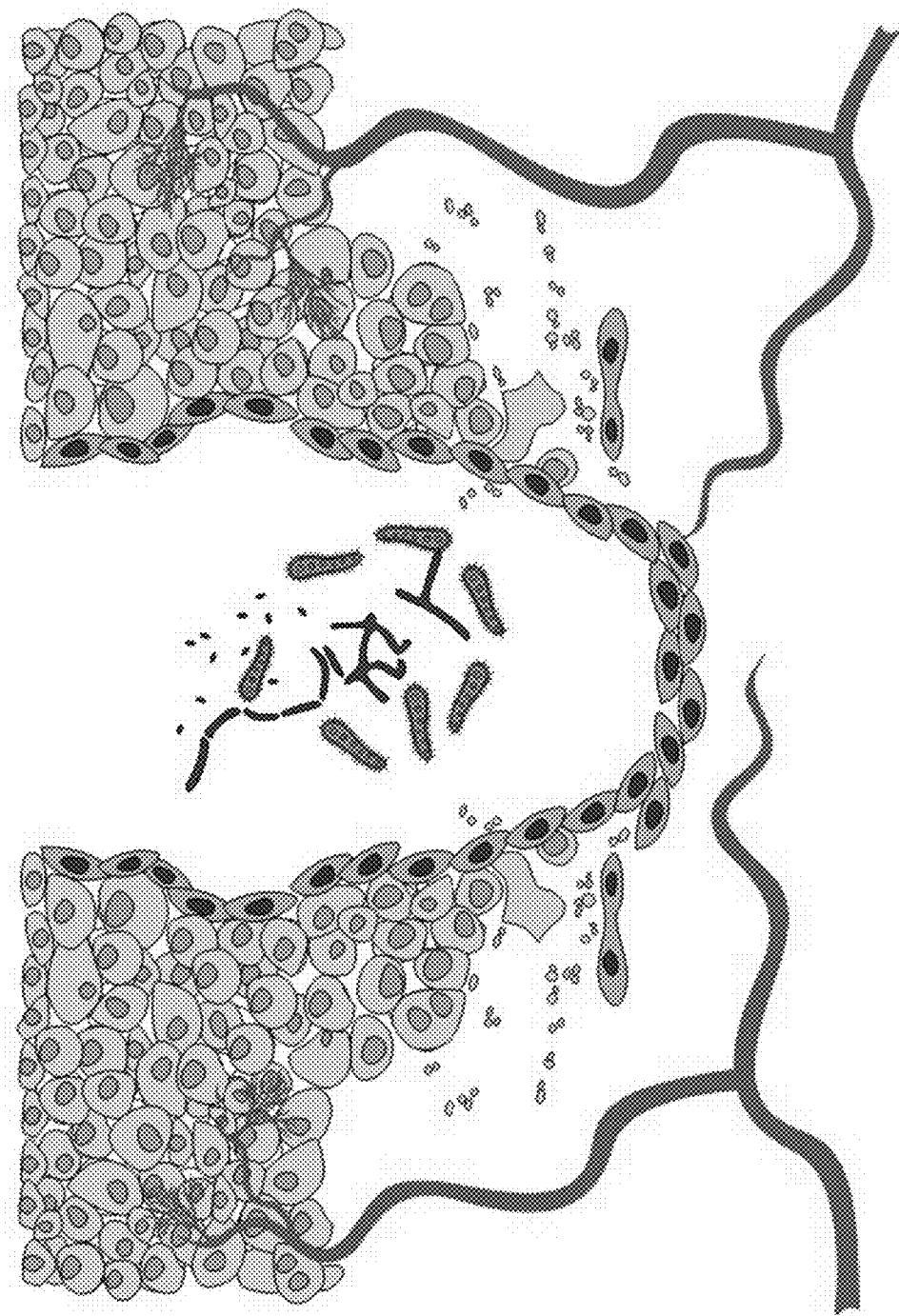
FIG. 1 is a transversal representation of a skin wound or ulcer. Before the treatment with MRJP1, a bacterial infection is present as well as low numbers of fibroblasts and blood vessels.
Figure 2:
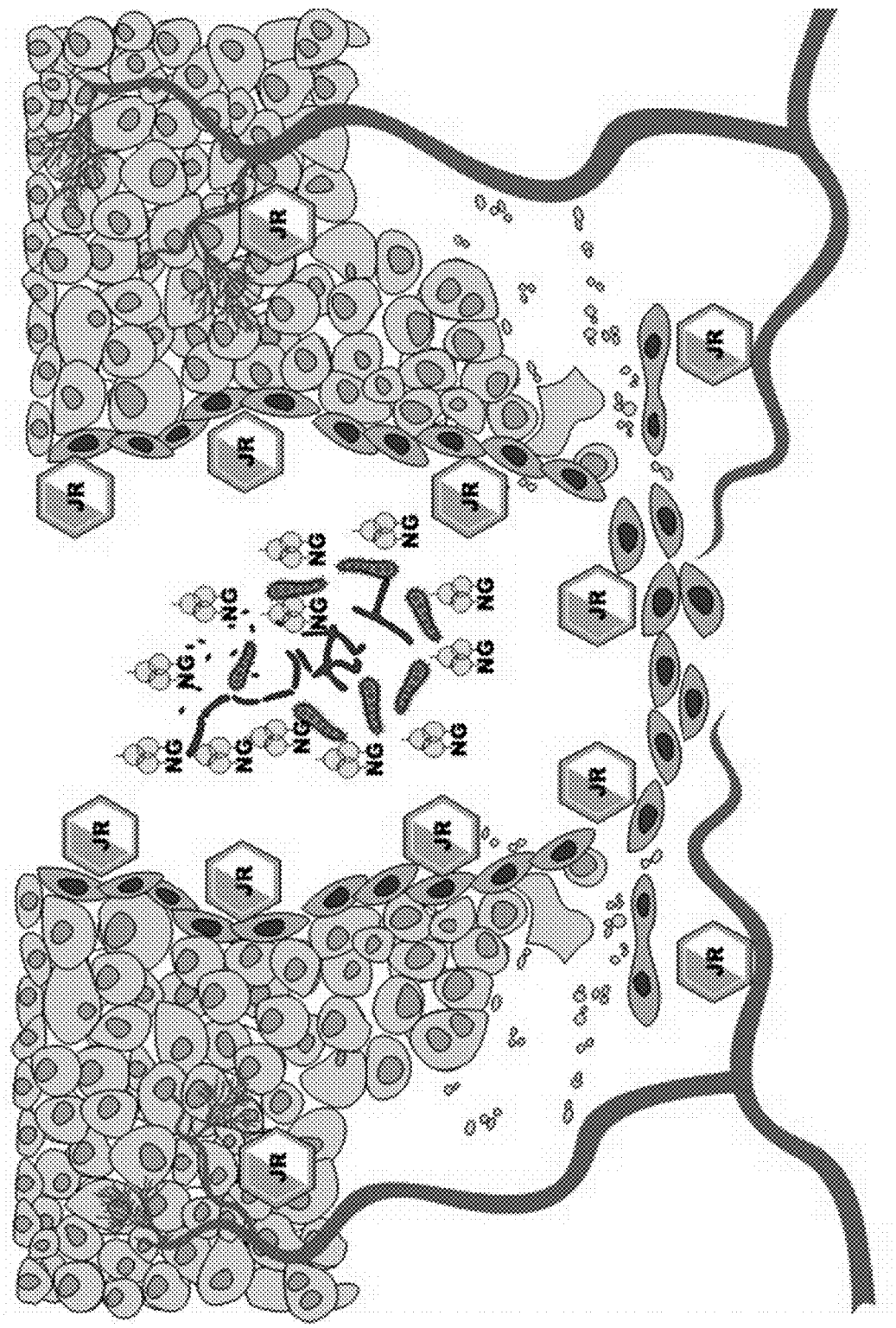
FIG. 2 is a representation of FIG. 1 except now MRJP1 is shown binding to the cell surface of fibroblasts, stimulating EGFR and promoting cell division. As an example of a bactericide that can be incorporated in the formulation, gold nanoparticles (NG) are shown binding to bacteria.
Figure 3:
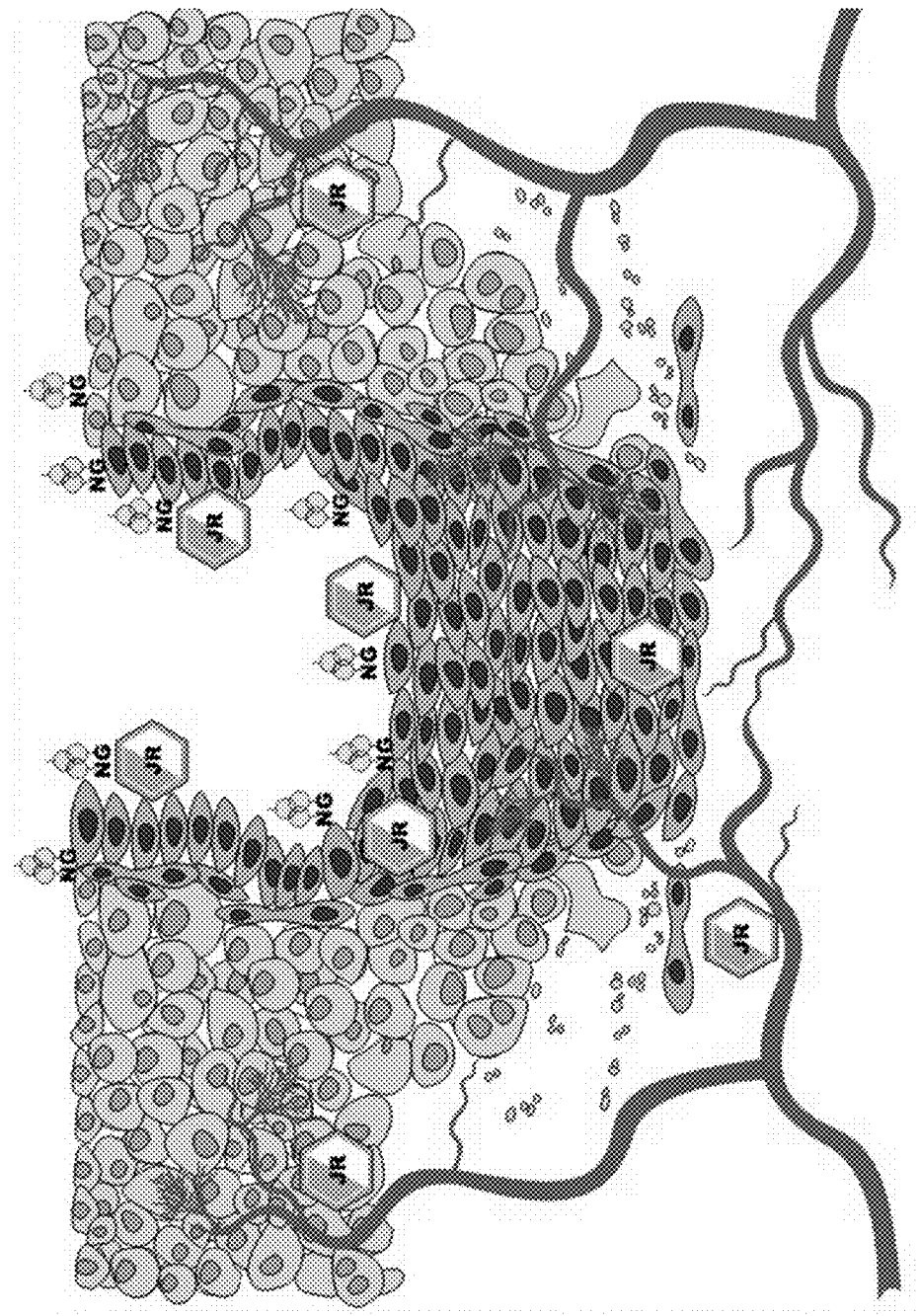
FIG. 3 is a transversal representation of a skin wound or ulcer after treatment with Topical MRJP1, new fibroblasts and blood vessels have formed which promote wound healing. Also, the gold nanoparticles (NG) have depleted the infection.

By isolating the effective component of royal jelly, major royal jelly protein 1 (MRJP1), and adding it to another composition in an effective concentration, a pharmaceutical composition that enhances tissue granulation, re-epithelialization and vascularization is obtained. MRJP1 in sufficient amounts may be used to treat mechanical, surgical, ischemic, infectious, or neuropathic skin wounds or ulcers. Additionally, topical MRJP1 may be used in mechanical injuries of the skin, vascular angiology, surgery recovery, dermatological disorders, burn treatment, reconstructive surgery, geriatric medicine, treatment of gangrenes and cosmetics.

The problem with other therapeutics attempting to use royal jelly is that other major royal jelly proteins that are not as effective as MRJP1 are kept in solution near a wound site. Additionally, other large chemicals such as sugars, fats, oils and other proteins are kept in solution as well. These other chemicals not only necessitate a smaller concentration of MRJP1, but also interfere with MRJP1 interacting with necessary proteins to aid in healing. Utilizing an effective amount of MRJP1 solves the problem of royal jellies and other pharmaceutical compositions that do not significantly aid in healing.

MRJP1 when isolated can be found in monomer or oligomer form. Depending on the topical pharmaceutical being produced, it may be advantageous to adjust the proportion of MRJP1 monomer to MRJP1 oligomer. Some topical formulations of MRJP1 may require a higher proportion of oligomer MRJP1 to monomer MRJP1 whereas in others the case may be reversed. As a general rule, the more oligomers of MRJP1 in solution, the more enhanced the healing will be.

MRJP1 stimulates cell proliferation by binding to the epidermal growth factor receptor (EGFR) of human cells. Epidermal growth factor receptors are a transmembrane protein found in cells making up epithelial tissue. MRJP1 displays a unique ability to interact with EGFR in humans and stimulate growth of epidermal cells. Although royal jellies often have different content compositions, some have 60-70% water, 12-15% proteins (including MRJPs), 10-16% sugar, and 3-6% lipids, vitamins, salts, and free amino acids. This means that when royal jelly is rubbed on a wound very little if any MRJP1 actually interacts with epithelial cells. If other royal jelly proteins or molecules are at a wound site, they may compete to bind, interact, or even block EGFR receptors. Even if other molecules show no binding affinity to EGFR, they may denature or interact with MRJP1, causing less MRJP1 to be available to interact with EGFR. Rather than apply royal jelly to a wound in the hopes that some MRJP1 gets to some receptors, a more effective therapy is to isolate the actual protein responsible for wound healing (MRJP1) and apply that protein in an effective dosage to actually bring about useful results.

Additionally, MRJP1 has been found to have bacteriostatic effects. Not only does MRJP1 stimulate EGFR, but MRJP1 can inhibit pathogens from causing infections at a wound site. Inhibiting infections at a wound site further aids in healing because the body's resources are spent growing new cells and tissue rather than fighting pathogens.

Adding MRJP1 alone to a wound site is an effective treatment. Other effective treatments involve combining an effective amount of MRJP1 with an acceptable pharmaceutical or cosmetic product. Whatever product is used must ensure that MRJP1 protein is not denatured, or if some MRJP1 is denatured, that enough MRJP1 remains able to interact with EGFR when introduced to a wound site.

An effective amount of MRJP1 can be added to various topical pharmaceutical compounds such as creams, lotions, ointments and other substances discussed below. This "topical MRJP1" could then be applied to a wound area for enhanced healing. A pharmaceutical formulation of topical MRJP1 should include 1-10,000 mg/L of isolated MRJP1 to be effective. In other circumstances, so long as MRJP1 is 1-10% the weight of the end product, topical MRJP1 will retain its efficacy. In human patients, application of topical MRJP1 containing 1-10,000 mg/L MRJP1 to a wound, may yield an up to 300% increase in the speed of healing. Patients undergoing treatment may also exhibit an increase in cell proliferation, cell migration, and vascularization. MRJP1 also increases re-epithelialization and granulation, which further helps with wound healing.

MRJP1 may be added alone to other topical pharmaceutical compounds as to maximize the amount of MRJP1 available to interact with EGFR. Other times, it may be beneficial to add MRJP1 to only a limited number of other chemicals that do not negatively interact with MRJP1 as to affect its binding affinity to EGFR. In other instances, already available cosmetic or pharmaceutical products may be fortified with MRJP1.

MRJP1 may be incorporated into other topical pharmaceuticals. Topical pharmaceuticals include creams, powders, dressings, liquids, ointments, gels, sunscreens, chap sticks, aerosols, sprays, nose, ear and eye drops, lotions, lozenges, paints, sprays and pastilles. MRJP1 may also be ingested orally as in a pill or tablet. In certain cases, MRJP1 alone may be added to the wound without any additives or in combination with any other compositions. MRJP1 can also be injected into a wound site or other parts of the body.

It may be beneficial to lyophilize (freeze dry) MRJP1 before adding it to certain topical formulations. To lyophilize MRJP1, MRJP1 should be isolated from other proteins or compounds and suspended in distilled water or an appropriate buffer solution. The isolated MRJP1 may then be freeze dried in a freezer. The entire lyophilization process may be done at 4° C. The lyophilization process can also start at a lower temperature, and gradually be heated up to 4° C. Once lyophilized, the lyophilized MRJP1 may be added to the compositions discussed below. In other instances, lyophilized MRJP1 may simply be introduced to a wound.

MRJP1 may be combined with a powder to create an effective powder formulation of MRJP1. This powder formulation may be applied to a wound site for enhanced healing. An example powder formulation of MRJP1 could be made by combining 1%-10% by weight lyophilized or non-lyophilized MRJP1, with 90%-99% dusting agent. Appropriate dusting agents include, talcum powder, cornstarch, cellulose products, sodium bicarbonate, montmorillonite, bentonite, leaf or other plant cell extract, ulmus fulva bark powder, rosa centifolia flower extract, and limonene. Dusting agents may either be combined with MRJP1 alone or in combination with other dusting agents and additives. For example, one effective powder formulation may be obtained by combining 10% lyophilized MRJP1, 83% talcum powder and 7% plant cell extract all by weight. Conventional solid makeups such as foundation and cover-up may also constitute a dusting agent.

MRJP1 may also be administered through, gels, creams, lotions, and ointments, to create an MRJP1 rub. The major difference between gels, creams, lotions, and ointments may either be the viscosity of the final product, or the entire formulation. Thus, a formulation appropriate for an ointment may be very similar to a lotion, the major difference being the lotion has more water or comparable liquid in it, making the final topical compound less viscous while the ointment has less water or comparable liquid in it, making it more viscous. Other times a lotion may have an almost entirely different chemical composition than the ointment (except for the addition of MRJP1). For example, an appropriate MRJP1 formulation for an ointment could consist of, zinc oxide, cetearyl alcohol, ceteareth-20, cetyl alcohol, glyceryl stearate, titanium dioxide, castor oil, bentonite, phenoxyethanol, iron oxides, and MRJP1, while an appropriate formulation of skin lotion for MRJP1, could consist of olive oil, castor oil, and MRJP1. However, note that by increasing the amount of castor oil in the skin lotion solution, one can obtain an ointment by the same formula because castor oil would make the lotion thicker.

A topical MRJP1 cream may be obtained by combining an effective amount of MRJP1 with creaming agent. Suitable creaming agents include sorbitan monooleate, sorbitan sequioleate, sorbitan trioleate, glyceryl stearate, sorbitan stearate, sorbitan tristearate, glycerin, glycerol, olive oil, triethanolamine, honey, carbomer, emulsifying wax, cetyl alcohol, quaternium, phenoxyethanol, benzyl salicylate, limonene, linalool, and beeswax. Additionally, effective creaming agents may be creams already on the market that would not denature proteins or MRJP1.

One potential formulation for an MRJP1 cream would be 1⅔ cup vegetable oil, ⅓ cup MRJP1 solution, 3 tbs cocoa butter, 6 tsp glycerin, 1⅔ aloe vera juice, 1½ tsp borax, and 2 tsp rosemary extract.

Other topical formulations include eye drops, and nose drops. A lyophilized version of MRJP1 can be placed in a solution of commercial eye drops or nose drops. In other instances, MRJP1 can be suspended in a solution of artificial tears. MRJP1 may also be combined with corticosteroids to enhance uptake in the nasal cavity and eyes. Fluticasone and triamcinolone may be used with MRJP1 without effecting MRJP1's efficacy. Other topical formulations include wound dressings such as gauze, tape, and bandages. To make a wound dressing, the dressing must be impregnated with MRJP1, and the MRJP1 must be allowed to diffuse to a wound site when applied near the wound. In one formulation MRJP1 may be added to hydrogel to create a dressing that when applied to a wound releases MRJP1. Lyophilized or non-lyophilized MRJP1 may be also be added to bandages, or gauze. A wound dressing may be soaked in a solution of MRJP1 and either dried then applied or applied directly to a wound site.

In other instances, MRJP1 can be suspended in water or an appropriate buffer, then added to a topical pharmaceutical or simply applied to a wound site. Appropriate buffers include phosphate buffer saline (20 mM Na2HPO4, 2 mM NaH2PO4.2H2O and 150 mM NaCl). Other buffers include Tris-acetate-EDTA, Tris-borate-EDTA, Tris-glycine buffer, SDS-Tris-glycine buffer, 4× Tris/SDS, and Tris-Tricine. An appropriate buffer should be kept at a pH of 7.4-8.0 to maximize MRJP1 efficacy.

When suspended in water or put in a buffer, a solution of MRJP1 may be combined with an aerosol and applied to a wound site. The solution of MRJP1 may also be put into a spray applicator such as a spray bottle and then sprayed on a wound as well.

Some users of topical MRJP1 may find it difficult to incorporate a new topical pharmaceutical into their daily routine. In this case, MRJP1 can be added to an already existing and purchased pharmaceutical or cosmetic product that the user already applies. For example, many people purchase moisturizers such as Neutrogena Hydro Boost® or acne creams such as Keeva®. An effective amount of MRJP1 may be mixed with these products before use to enhance the healing effects of those products. Additionally, MRJP1 may be incorporated into a cosmetic facemask. Along with being composed of the lotions and creams disclosed, facemasks may also be made from minerals, vitamins, fruit extracts, clays, and mud. MRJP1 may either be applied to the skin before the application of a mask or be applied to the material making the mask.

It may be appropriate to infuse other additives with a topical formulation of MRJP1. These additives may either enhance healing or have other perceived health benefits. Appropriate additives include vitamin A, vitamin C, vitamin D, vitamin E, vitamin K, thiamine, riboflavin, niacin, pantothenic acid, biotin, vitamin B-6, vitamin B-12 folate, gold nano particles, minerals including calcium, chloride, magnesium, phosphorus, potassium, sodium, and sulfur. Corticosteroids may also be added. In other formulations antibiotics may also be added. A proper pharmaceutical incorporating MRJP1 should not have so many other proteins or large molecules in it, that MRJP1 can no longer interact with EGFR.

Often times wound sites may become infected. Thus, including other compounds that reduce infection such as bactericides may be beneficial. Other additives include analgesic, anti-inflammatory and/or antiseptic compounds. More specifically, chlorhexidine, povidone-iodine, iodine, chloroxylenol, benzalkonium chloride, hexachlorophene, polyhexanide, acriflavine, merbromin, and sodium hypochlorite may be added in diluted forms.

MRJP1 successfully stimulates skin growth. Still, in certain topical formulations it may be beneficial to combine MRJP1 with other molecules that stimulate skin growth, or skin growth factors. Skin growth factors may be other proteins or biologically produced molecules such as adrenomedullin, angiopoietin, autocrine motility factor, bone morphogenetic proteins, ciliary neurotrophic factor, leukemia inhibitory factor, interleukin-6 (IL-6), colony-stimulating factors, macrophage colony-stimulating factor (M-CSF), granulocyte colony-stimulating factor (G-CSF), granulocyte macrophage colony-stimulating factor (GM-CSF), epidermal growth factor (EGF), ephrins, erythropoietin, fibroblast growth factor, foetal bovine somatotrophin, neurturin, persephin, artemin, neuregulins, placental growth factor, T-cell growth factor, thrombopoietin, transforming growth factors, and vascular endothelial growth factor. Note, the skin factors above although mostly human in origin may be obtained from non-human organisms. Synthetic or non-synthetic growth factors are appropriate in most cases. Additionally, growth factors may be synthesized in a lab or harvested from an organism, or grown in cell culture.

If MRJP1 is not available, then other major royal jelly proteins may be used in concentrated form to enhance healing. For example, a concentration of major royal jelly protein 2 in concentration of 1-10,000 mg/L or 1-10% MRJP1 by weight may also lead to enhanced healing. The same is true for major royal jelly proteins 3-9. Note however MRJP1 will likely yield the best results in comparison to other concentrated royal jellies.

MRJP1 may also be administered though injection or intravenous drip. MRJP1 can also be introduced to endosomes or nanocarriers which can either be applied to the skin or bloodstream. However, using topical MRJP1 treatment may be less painful because injections often need to pierce the skin. Additionally, whereas injections are usually administered by medical personnel, topical MRJP1 can be administered by a patient themselves without the need for highly trained staff or cumbersome doctor visits.

MRJP1 added to topical pharmaceuticals is superior to other treatments not only because it makes wounds heal faster, but because its use reduces other negative impacts associated with conventional treatment. For example, the cost of healthcare can be reduced because patients spend less time in the hospital when their wounds heal faster. Additionally, patients may take less trips to the hospital if their wounds heal faster. Unlike most topical pharmaceuticals, topical MRJP1 not only stimulates re-epithelialization but also granulation and vascularization of an affected area of the body. This makes MRJP1 a unique component for pharmaceutical formulations for the treatment of skin wounds or ulcers of any type or etiology.

A sufficient concentration of MRJP1 can be obtained by isolating MRJP1 from royal jelly produced by a bee hive. MRJP1 can also be obtained by organic or other chemical synthesis. MRJP1 can also be produced through biotechnology production methods. Recombinant DNA technology can be used to create transgenic prokaryotic or eukaryotic cells. Bacteria, yeast, fungi, algae, microalgae animals, plant, vegetables or their cultured cells can then produce MRJP1 in an adequate amount to produce a concentration sufficient for a pharmaceutical solution of MRJP1. Experimental evolution techniques such as adaptive evolution could also be used to either give an organism the ability to or enhance an organism's capabilities of producing MRJP1. Another method of producing MRJP1 is to create knockout versions of bees that only express MRJP1 and no other major royal jelly proteins. RNAi, and CRISPR can be used to silence genes coding for all major royal jelly proteins besides MRJP1. Additionally, MRJP1 genes can be upregulated using a strong promoter to increase production of MRJP1. Rather than delete other major royal jelly proteins, major royal jelly proteins 2-9 could simply be replaced by MRJP1 genes to increase production of MRJP1.

Genetic sequences from the following organisms may be used to create MRJP1 through biotechnological processes, *Apis mellifera, Apis cerana, Bactrocera dorsalis, Ceratitis capitate, Apis dorsata, Zeugodacus cucurbitae,* and *Aedes albopictus.*

Genetic sequences that code for the following amino acids may be used to create MRJP1.

```
Sequence 1:
MTRLFMLVCLGIVCQGTTGNILRGESLNKSLPILHEWKFFDYDFGSDERR

QDAILSGEYDYKNNYPSDIDQWHDKIFVTMLRYNGVPSSLNVISKKVGDG

GPLLQPYPDWSFAKYDDCSGIVSASKLAIDKCDRLWVLDSGLVNNTQPMC

SPKLLTFDLTTSQLLKQVEIPHDVAVNATTGKGRLSSLAVQSLDCNTNSD

TMVYIADEKGEGLIVYHNSDDSFHRLTSNTFDYDPKFTKMTIDGESYTAQ

DGISGMALSPMTNNLYYSPVASTSLYYVNTEQFRTSDYQQNDIHYEGVQN

ILDTQSSAKVVSKSGVLFFGLVGDSALGCWNEHRTLERHNIRTVAQSDET

LQMIASMKIKEALPHVPIFDRYINREYILVLSNKMQKMVNNDFNFDDVNF

RIMNANVNELILNTRCENPDNDRTPFKISIHL

Sequence 2:
MTRWLFMVVCLGIVCQGTTSSILRGESLNKSLSVLHEWKFFDYDFDSDER

RQDAILSGEYDYRKNYPSDVDQWHGKIFVTMLRYNGVPSSLNVISKKIGD

GGPLLQPYPDWSFAKYDDCSGIVSATKLAIDKCDRLWVLDSGLVNNTQPM

CSPKLLTFDLTTSQLLKQVEIPHDVAVNATTGKGRLSSLAVQPLDCNING

DTMVYIADEKGEGLIVYHDSDNSFHRLTSKTFDYDPKFTKMTINGESFTT

QSGISGMALSPMTNNLYYSPVASTSLYYVNTEQFRTSNYEQNAVHYEGVQ

NILDTQSSAKVVSKSGVLFFGLVGDSALGCWNEHRSLERHNIRTVAQSDE

TLQMIVGMKIKEALPHVPIFDRYINREYILVLSNRMQKMANNDYNFNDVN

FRIMDANVNDLILNTRCENPNNDNTPFKISIHL

Sequence 3:
MRALQSLVCTALALACVLASDDDKDMEPVIWTGGETLDPRTGQTHFNGLA

TRCQIHEHWGFVAIPKLKPDVQSSCAKLDMRKQIGVQTKHILTPFPPNEP

TDPQSPKRLQSVVDLCIDHLNSVWVLDVGAIYPPKNEDDPTPIICHPKIC

AYNAADGKLRFDMNLLPYVGPMSRLQFINVDYDEHGDPFVHVSDAGTKAL

IVCDVKRNTCHRVELPEDVISDYAPRDVLYTVLVRKANGRNKLYFTYRSG

ESLWCVNTQDLQKDKSCSKAWVVGKKEHKMIILGTDDWESMYFRWEENTK
```

```
EVYKWNTETAFDSKNFLLVHKSHTDLTPTHAMADYKNGVMRICLGNLIDY

LKHDTHTKEAKNSLEVMAIGDEPSPSSHLGHSGMREL
```

MRJP1 may also be applied in a "probiotic" form. A probiotic form would comprise a microorganism either naturally expressing or engineered to express MRJP1 either intracellularly, or extracellularly. Suitable microorganisms include bacteria already naturally living in humans including, *Acinetobacter calcoaceticus, Burkholderia cepacia, Pseudomonas pseudoalcaligenes, Fusobacterium necrophorum, Staphylococcus aureus,* and *Staphylococcus epidermidis.* In particular, it may be even more beneficial to select a microorganism that normally lives on human skin to express MRJP1. Some of these species and specific organisms include, *Bacillus, Candida albicans, Corynebacterium, Corynebacterium parvum, Demodex folliculorum, Enterobacter cloacae, Epidermophyton floccosum, Micrococcus, Micrococcus luteus, Mycobacterium, Neisseria, Peptostreptococcus, Malassezia ovale, Propionibacterium, Propionibacterium acnes, Pseudomonas aeruginosa, Sarcina, Staphylococcus aureus, Staphylococcus epidermidis, Staphylococcus haemolyticus, Streptococcus viridans, Trichophyton.* In other embodiments, organisms besides bacteria such as yeast and fungi may be engineered to express MRJP1 while residing on a human body.

MRJP1 in probiotic form may either be applied directly to a wound site, ingested, or injected into a human. The benefit of MRJP1 applied in probiotic form to a wound site may be twofold. First, the MRJP1 produced by the organism will benefit a wound for the reasons described above. Second, the organisms producing MRJP1 if near or on a wound will crowd out the surface space by being present there. This means that other harmful organisms that would usually infect a wound site would be unable to cause an infection, because the space the infectious organisms would occupy has literally already been taken up by beneficial organisms expressing MRJP1.

MRJP1 can also be obtained by isolating it from royal jelly. Appropriate methods for isolating MRJP1 from the other chemicals in royal jelly include ultrafiltration, liquid-liquid extraction, ultracentrifugation, centrifugation, chromatography, ion-exchange, and gel filtration chromatography. Additionally, straining royal jelly may also be able to separate MRJPs from one another. Fractionation of the MRJPs on DEAE cellulose may also be used. Royal Jelly proteins may also be centrifuged to separate them from one another. A combination of the above filtration methods may also be used.

MRJP1 should not exceed a final concentration of 10,000 mg/L or 1%-10% MRJP1 by weight when added to any other pharmaceutical or used in treatment. A higher concentration may produce adverse side effects. Although a concentration of 1 mg/L may be enough to bring beneficial results, compositions should strive to include a concentration above 1 mg/L.

It should be noted that MRJP1 itself may have a short shelf life. However, when combined with other pharmaceutical compounds MRJP1 will retain its efficacy for two years if kept in room temperature storage. Lyophilized MRJP1 will retain its shelf life faster than MRJP1 stored in solution. This is important for reducing the cost and transportation of the formulation. As a general rule, MRJP1 formulations should be kept in a refrigerator or cold area to increase shelf life. Topical MRJP1 is suitable for use in humans, veterinary care, and experimental medicine.

Depending on the wound, topical MRJP1 should be applied at different frequencies. As a general rule, MRJP1 in a cream is better for dry ulcers exhibiting normal or moderate exudation. MRJP1 with powder or aerosol may be better for treating ulcers exhibiting high exudation. Applying a topical formulation of MRJP1 once per day may be enough. For some wounds, once every other day, once every three days, two to three times per week or once per week may be appropriate. Generally, MRJP1 should be applied whenever a wound dressing is changed, or wound cleaning takes place. As a general rule the more severe the wound, the higher the frequency of MRJP1 applications. In other cases, simply applying topical MRJP1 liberally will enhance healing. In other instances, a topical form of MRJP1 can be integrated into a person's own skincare routine. For example, if someone applies acne cream twice a day (once in the morning and once at night) they can also apply topical MRJP1 once in the morning and once at night. If recommended or prescribed by a doctor, patients or users of MRJP1 should apply MRJP1 according to the doctor's instructions.

For enhanced results a wound should be cleaned and disinfected before applying Topical MRJP1. Wound cleaning will often depend on the wound. For example, depending on the severity of a burn wound, dead skin will likely need to be removed to clean the wound. If possible, debridement should occur before the application of topical MRJP1. The severity and type of ulcer will also mandate cleaning before applying topical MRJP1.

As used herein, "plurality" means two or more. As used herein, a "set" of items may include one or more of such items. As used herein, whether in the written description or the claims, the terms "comprising", "including", "carrying", "having", "containing", "involving", and the like are to be understood to be open-ended, i.e., to mean including but not limited to. Only the transitional phrases "consisting of" and "consisting essentially of", respectively, are closed or semi-closed transitional phrases with respect to claims. Use of ordinal terms such as "first", "second", "third", etc., in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements. As used herein, "and/or" means that the listed items are alternatives, but the alternatives also include any combination of the listed items.

SEQUENCE LISTING

<160> NUMBER OF SEQ ID NOS: 3

<210> SEQ ID NO 1
<211> LENGTH: 432
<212> TYPE: PRT
<213> ORGANISM: Apis mellifera

<400> SEQUENCE: 1

Met Thr Arg Leu Phe Met Leu Val Cys Leu Gly Ile Val Cys Gln Gly
1               5                   10                  15

Thr Thr Gly Asn Ile Leu Arg Gly Glu Ser Leu Asn Lys Ser Leu Pro
            20                  25                  30

Ile Leu His Glu Trp Lys Phe Phe Asp Tyr Asp Phe Gly Ser Asp Glu
        35                  40                  45

Arg Arg Gln Asp Ala Ile Leu Ser Gly Glu Tyr Asp Tyr Lys Asn Asn
    50                  55                  60

Tyr Pro Ser Asp Ile Asp Gln Trp His Asp Lys Ile Phe Val Thr Met
65                  70                  75                  80

Leu Arg Tyr Asn Gly Val Pro Ser Ser Leu Asn Val Ile Ser Lys Lys
                85                  90                  95

Val Gly Asp Gly Gly Pro Leu Leu Gln Pro Tyr Pro Asp Trp Ser Phe
            100                 105                 110

Ala Lys Tyr Asp Asp Cys Ser Gly Ile Val Ser Ala Ser Lys Leu Ala
        115                 120                 125

Ile Asp Lys Cys Asp Arg Leu Trp Val Leu Asp Ser Gly Leu Val Asn
    130                 135                 140

Asn Thr Gln Pro Met Cys Ser Pro Lys Leu Leu Thr Phe Asp Leu Thr
145                 150                 155                 160

Thr Ser Gln Leu Leu Lys Gln Val Glu Ile Pro His Asp Val Ala Val
                165                 170                 175

Asn Ala Thr Thr Gly Lys Gly Arg Leu Ser Ser Leu Ala Val Gln Ser
            180                 185                 190

Leu Asp Cys Asn Thr Asn Ser Asp Thr Met Val Tyr Ile Ala Asp Glu
        195                 200                 205

Lys Gly Glu Gly Leu Ile Val Tyr His Asn Ser Asp Asp Ser Phe His
210                 215                 220

Arg Leu Thr Ser Asn Thr Phe Asp Tyr Asp Pro Lys Phe Thr Lys Met
225                 230                 235                 240

Thr Ile Asp Gly Glu Ser Tyr Thr Ala Gln Asp Gly Ile Ser Gly Met
                245                 250                 255

Ala Leu Ser Pro Met Thr Asn Asn Leu Tyr Tyr Ser Pro Val Ala Ser
            260                 265                 270

Thr Ser Leu Tyr Tyr Val Asn Thr Glu Gln Phe Arg Thr Ser Asp Tyr
        275                 280                 285

Gln Gln Asn Asp Ile His Tyr Glu Gly Val Gln Asn Ile Leu Asp Thr
290                 295                 300

Gln Ser Ser Ala Lys Val Val Ser Lys Ser Gly Val Leu Phe Phe Gly
305                 310                 315                 320

Leu Val Gly Asp Ser Ala Leu Gly Cys Trp Asn Glu His Arg Thr Leu
                325                 330                 335

Glu Arg His Asn Ile Arg Thr Val Ala Gln Ser Asp Glu Thr Leu Gln
            340                 345                 350

Met Ile Ala Ser Met Lys Ile Lys Glu Ala Leu Pro His Val Pro Ile
        355                 360                 365

Phe Asp Arg Tyr Ile Asn Arg Glu Tyr Ile Leu Val Leu Ser Asn Lys
370                 375                 380

Met Gln Lys Met Val Asn Asn Asp Phe Asn Phe Asp Asp Val Asn Phe
385                 390                 395                 400

Arg Ile Met Asn Ala Asn Val Asn Glu Leu Ile Leu Asn Thr Arg Cys
                405                 410                 415

Glu Asn Pro Asp Asn Asp Arg Thr Pro Phe Lys Ile Ser Ile His Leu
            420                 425                 430

<210> SEQ ID NO 2
<211> LENGTH: 433
<212> TYPE: PRT
<213> ORGANISM: Apis mellifera

<400> SEQUENCE: 2

Met Thr Arg Trp Leu Phe Met Val Val Cys Leu Gly Ile Val Cys Gln
1               5                   10                  15

Gly Thr Thr Ser Ser Ile Leu Arg Gly Glu Ser Leu Asn Lys Ser Leu
            20                  25                  30

Ser Val Leu His Glu Trp Lys Phe Phe Asp Tyr Asp Phe Asp Ser Asp
        35                  40                  45

Glu Arg Arg Gln Asp Ala Ile Leu Ser Gly Glu Tyr Asp Tyr Arg Lys
50                  55                  60

Asn Tyr Pro Ser Asp Val Asp Gln Trp His Gly Lys Ile Phe Val Thr
65                  70                  75                  80

Met Leu Arg Tyr Asn Gly Val Pro Ser Ser Leu Asn Val Ile Ser Lys
                85                  90                  95

Lys Ile Gly Asp Gly Gly Pro Leu Leu Gln Pro Tyr Pro Asp Trp Ser
            100                 105                 110

Phe Ala Lys Tyr Asp Asp Cys Ser Gly Ile Val Ser Ala Thr Lys Leu
        115                 120                 125

Ala Ile Asp Lys Cys Asp Arg Leu Trp Val Leu Asp Ser Gly Leu Val
130                 135                 140

Asn Asn Thr Gln Pro Met Cys Ser Pro Lys Leu Leu Thr Phe Asp Leu

```
                145                 150                 155                 160
Thr Thr Ser Gln Leu Leu Lys Gln Val Glu Ile Pro His Asp Val Ala
                165                 170                 175
Val Asn Ala Thr Thr Gly Lys Gly Arg Leu Ser Ser Leu Ala Val Gln
                180                 185                 190
Pro Leu Asp Cys Asn Ile Asn Gly Asp Thr Met Val Tyr Ile Ala Asp
                195                 200                 205
Glu Lys Gly Glu Gly Leu Ile Val Tyr His Asp Ser Asp Asn Ser Phe
            210                 215                 220
His Arg Leu Thr Ser Lys Thr Phe Asp Tyr Asp Pro Lys Phe Thr Lys
225                 230                 235                 240
Met Thr Ile Asn Gly Glu Ser Phe Thr Thr Gln Ser Gly Ile Ser Gly
                245                 250                 255
Met Ala Leu Ser Pro Met Thr Asn Asn Leu Tyr Tyr Ser Pro Val Ala
                260                 265                 270
Ser Thr Ser Leu Tyr Tyr Val Asn Thr Glu Gln Phe Arg Thr Ser Asn
            275                 280                 285
Tyr Glu Gln Asn Ala Val His Tyr Glu Gly Val Gln Asn Ile Leu Asp
            290                 295                 300
Thr Gln Ser Ser Ala Lys Val Val Ser Lys Ser Gly Val Leu Phe Phe
305                 310                 315                 320
Gly Leu Val Gly Asp Ser Ala Leu Gly Cys Trp Asn Glu His Arg Ser
                325                 330                 335
Leu Glu Arg His Asn Ile Arg Thr Val Ala Gln Ser Asp Glu Thr Leu
                340                 345                 350
Gln Met Ile Val Gly Met Lys Ile Lys Glu Ala Leu Pro His Val Pro
                355                 360                 365
Ile Phe Asp Arg Tyr Ile Asn Arg Glu Tyr Ile Leu Val Leu Ser Asn
                370                 375                 380
Arg Met Gln Lys Met Ala Asn Asn Asp Tyr Asn Phe Asn Asp Val Asn
385                 390                 395                 400
Phe Arg Ile Met Asp Ala Asn Val Asn Asp Leu Ile Leu Asn Thr Arg
                405                 410                 415
Cys Glu Asn Pro Asn Asn Asp Asn Thr Pro Phe Lys Ile Ser Ile His
                420                 425                 430
Leu

<210> SEQ ID NO 3
<211> LENGTH: 387
<212> TYPE: PRT
<213> ORGANISM: Apis mellifera

<400> SEQUENCE: 3

Met Arg Ala Leu Gln Ser Leu Val Cys Thr Ala Leu Ala Leu Ala Cys
1               5                   10                  15
Val Leu Ala Ser Asp Asp Lys Asp Met Glu Pro Val Ile Trp Thr
                20                  25                  30
Gly Gly Glu Thr Leu Asp Pro Arg Thr Gly Gln Thr His Phe Asn Gly
            35                  40                  45
Leu Ala Thr Arg Cys Gln Ile His Glu His Trp Gly Phe Val Ala Ile
            50                  55                  60
Pro Lys Leu Lys Pro Asp Val Gln Ser Ser Cys Ala Lys Leu Asp Met
65                  70                  75                  80
Arg Lys Gln Ile Gly Val Gln Thr Lys His Ile Leu Thr Pro Phe Pro
```

```
                        85                  90                  95
Pro Asn Glu Pro Thr Asp Pro Gln Ser Pro Lys Arg Leu Gln Ser Val
                100                 105                 110
Val Asp Leu Cys Ile Asp His Leu Asn Ser Val Trp Val Leu Asp Val
                115                 120                 125
Gly Ala Ile Tyr Pro Pro Lys Asn Glu Asp Asp Pro Thr Pro Ile Ile
                130                 135                 140
Cys His Pro Lys Ile Cys Ala Tyr Asn Ala Ala Asp Gly Lys Leu Arg
145                 150                 155                 160
Phe Asp Met Asn Leu Leu Pro Tyr Val Gly Pro Met Ser Arg Leu Gln
                165                 170                 175
Phe Ile Asn Val Asp Tyr Asp Glu His Gly Asp Pro Phe Val His Val
                180                 185                 190
Ser Asp Ala Gly Thr Lys Ala Leu Ile Val Cys Asp Val Lys Arg Asn
                195                 200                 205
Thr Cys His Arg Val Glu Leu Pro Glu Asp Val Ile Ser Asp Tyr Ala
210                 215                 220
Pro Arg Asp Val Leu Tyr Thr Val Leu Val Arg Lys Ala Asn Gly Arg
225                 230                 235                 240
Asn Lys Leu Tyr Phe Thr Tyr Arg Ser Gly Glu Ser Leu Trp Cys Val
                245                 250                 255
Asn Thr Gln Asp Leu Gln Lys Asp Lys Ser Cys Ser Lys Ala Trp Val
                260                 265                 270
Val Gly Lys Lys Glu His Lys Met Ile Ile Leu Gly Thr Asp Asp Trp
                275                 280                 285
Glu Ser Met Tyr Phe Arg Trp Glu Glu Asn Thr Lys Glu Val Tyr Lys
                290                 295                 300
Trp Asn Thr Glu Thr Ala Phe Asp Ser Lys Asn Phe Leu Leu Val His
305                 310                 315                 320
Lys Ser His Thr Asp Leu Thr Pro Thr His Ala Met Ala Asp Tyr Lys
                325                 330                 335
Asn Gly Val Met Arg Ile Cys Leu Gly Asn Leu Ile Asp Tyr Leu Lys
                340                 345                 350
His Asp Thr His Thr Lys Glu Ala Lys Asn Ser Leu Glu Val Met Ala
                355                 360                 365
Ile Gly Asp Glu Pro Ser Pro Ser Ser His Leu Gly His Ser Gly Met
                370                 375                 380
Arg Glu Leu
385
```

It is claimed:

1. A method for enhancing the healing of a mechanical, surgical, ischemic, infectious, or neuropathic skin wound or ulcer in a patient in need thereof, consisting essentially of: administering to the wound or ulcer a therapeutically effective amount of isolated major royal jelly protein 1 (MRJP1), wherein the MRJP1 is the sequence (SEQ ID NO: 2)
MTRWLFMVVCLGIVCQGTTSSILRGESLNKSLSVLHEWKFFDYDFDSD

ERRQDAILSGEYDYRKNYPSDVDQWHGKIFVTMLRYNGVPSSLNVISK

KIGDGGPLLQPYPDWSFAKYDDCSGIVSATKLAIDKCDRLWVLDSGLV

NNTQPMCSPKLLTFDLTTSQLLKQVEIPHDVAVNATTGKGRLSSLAVQ

PLDCNINGDTMVYIADEKGEGLIVYHDSDNSFHRLTSKTFDYDPKFTK

MTINGESFTTQSGISGMALSPMTNNLYYSPVASTSLYYVNTEQFRTSN

YEQNAVHYEGVQNILDTQSSAKVVSKSGVLFFGLVGDSALGCWNEHRS

LERHNIRTVAQSDETLQMIVGMKIKEALPHVPIFDRYINREYILVLSN

RMQKMANNDYNFNDVNFRIMDANVNDLILNTRCENPNNDNTPFKISIHL or (SEQ ID NO: 3)
MRALQSLVCTALALACVLASDDDKDMEPVIWTGGETLDPRTGQTHFNGL

ATRCQIHEHWGFVAIPKLKPDVQSSCAKLDMRKQIGVQTKHILTPFPPN

EPTDPQSPKRLQSVVDLCIDHLNSVWVLDVGAIYPPKNEDDPTPIICHP

-continued

KICAYNAADGKLRFDMNLLPYVGPMSRLQFINVDYDEHGDPFVHVSDAG

TKALIVCDVKRNTCHRVELPEDVISDYAPRDVLYTVLVRKANGRNKLYF

TYRSGESLWCVNTQDLQKDKSCSKAWVVGKKEHKMIILGTDDWESMYFR

WEENTKEVYKWNTETAFDSKNFLLVHKSHTDLTPTHAMADYKNGVIVIR

ICLGNLIDYLKHDTHTLEAKNSLEVMAIGDEPSPSSHLGHSGMREL, and wherein the method is effective for treating the wound or ulcer.

2. A method for enhancing the healing of mechanical, surgical, ischemic, infectious, or neuropathic skin wounds or ulcers in a patient in need thereof, consisting essentially of: administering to the wound or ulcer a therapeutically effective amount of isolated major royal jelly protein 1 (MRJP1), wherein the MRJP1 is the sequence (SEQ ID NO: 2)
MTRWLFMVVCLGIVCQGTTSSILRGESLNKSLSVLHEWKFFDYDFDSD

ERRQDAILSGEYDYRKNYPSDVDQWHGKIFVTMLRYNGVPSSLNVISK

KIGDGGPLLQPYPDWSFAKYDDCSGIVSATKLAIDKCDRLWVLDSGLV

NNTQPMCSPKLLTFDLTTSQLLKQVEIPHDVAVNATTGKGRLSSLAVQ

PLDCNINGDTMVYIADEKGEGLIVYHDSDNSFHRLTSKTFDYDPKFTK

MTINGESFTTQSGISGMALSPMTNNLYYSPVASTSLYYVNTEQFRTSN

YEQNAVHYEGVQNILDTQSSAKVVSKSGVLFFGLVGDSALGCWNEHRS

LERHNIRTVAQSDETLQMIVGMKIKEALPHVPIFDRYINREYILVLSN

RMQKMANNDYNFNDVNFRIMDANVNDLILNTRCENPNNDNTPFKISIHL or (SEQ ID NO: 3)
MRALQSLVCTALALACVLASDDDKDMEPVIWTGGETLDPRTGQTHFNGL

ATRCQIHEHWGFVAIPKLKPDVQSSCAKLDMRKQIGVQTKHILTPFPPN

EPTDPQSPKRLQSVVDLCIDHLNSVWVLDVGAIYPPKNEDDPTPIICHP

KICAYNAADGKLRFDMNLLPYVGPMSRLQFINVDYDEHGDPFVHVSDAG

TKALIVCDVKRNTCHRVELPEDVISDYAPRDVLYTVLVRKANGRNKLYF

TYRSGESLWCVNTQDLQKDKSCSKAWVVGKKEHKMIILGTDDWESMYFR

WEENTKEVYKWNTETAFDSKNFLLVHKSHTDLTPTHAMADYKNGVMRIC

LGNLIDYLKHDTHTLEAKNSLEVMAIGDEPSPSSHLGHSGMREL;

and at least one analgesic, anti-inflammatory and/or antiseptic compound, wherein the method is effective for treating the wound or ulcer.

* * * * *